(12) United States Patent
Tonami

(10) Patent No.: US 8,712,715 B2
(45) Date of Patent: Apr. 29, 2014

(54) RADIATION IMAGING DEVICE

(75) Inventor: Hiromichi Tonami, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 429 days.

(21) Appl. No.: 13/132,150

(22) PCT Filed: Dec. 1, 2008

(86) PCT No.: PCT/JP2008/071781
§ 371 (c)(1),
(2), (4) Date: Jun. 1, 2011

(87) PCT Pub. No.: WO2010/064287
PCT Pub. Date: Jun. 10, 2010

(65) Prior Publication Data
US 2011/0238354 A1  Sep. 29, 2011

(51) Int. Cl.
*G06F 19/00* (2011.01)
*H05G 1/26* (2006.01)

(52) U.S. Cl.
USPC .......................................... 702/104; 378/163

(58) Field of Classification Search
USPC ............ 702/104, 86, 85; 378/4, 6, 7, 70, 162, 378/163, 164
See application file for complete search history.

(56) References Cited

U.S. PATENT DOCUMENTS

| | | | |
|---|---|---|---|
| 5,291,539 A | 3/1994 | Thumann et al. | |
| 5,581,592 A | 12/1996 | Zarnoch et al. | |
| 6,671,349 B1 * | 12/2003 | Griffith | 378/163 |
| 6,888,924 B2 * | 5/2005 | Claus et al. | 378/163 |
| 6,960,020 B2 * | 11/2005 | Lai | 378/207 |
| 7,494,277 B2 * | 2/2009 | Setala | 378/207 |
| 2001/0012330 A1 * | 8/2001 | Ogura et al. | 378/95 |
| 2004/0264648 A1 * | 12/2004 | Claus et al. | 378/163 |
| 2010/0135467 A1 * | 6/2010 | King et al. | 378/163 |

FOREIGN PATENT DOCUMENTS

JP    2001-134748    5/2001

* cited by examiner

*Primary Examiner* — Sujoy Kundu
*Assistant Examiner* — Ricky Ngon
(74) *Attorney, Agent, or Firm* — J.C. Patents

(57) ABSTRACT

Correction by moire elimination is carried out with high precision in an environment where relative misalignment among the focal point, the grid, and the X-ray flat panel detector may occur. A part of each of two signal regions of interest is masked by an X-ray plate, and an operation value $Rf=(Sx-Sy)/(Sx+Sy)$ is defined for signal values Sx and Sy obtained from the masked portions. By associating the operation value Rf with the relative position relationship, the relative position relationship is obtained from the operation value Rf, and a correction parameter for the relationship is used.

5 Claims, 8 Drawing Sheets

RADIATION IMAGING DEVICE

CROSS-REFERENCE TO RELATED APPLICATION

This application is a 371 of international application of PCT application serial no. PCT/JP2008/071781, filed on Dec. 1, 2008. The entirety of the above-mentioned patent application is hereby incorporated by reference herein and made a part of this specification.

BACKGROUND OF THE INVENTION

1. Field of the Invention

The invention relates to the correction of an X-ray flat panel detector and a grid for elimination of scattered ray, used in a radiation imaging device for medical use.

2. Description of Related Art

In recent years, solid-state imaging devices, which are also called "flat panel detector (FPD)," have drawn a lot of attention. It is known that the operating methods thereof include a direct-type FPD and an indirect-type FPD. The direct-type FPD converts X-ray energy into an electric charge directly, and the electric charge is read by a readout element, e.g. a thin film transistor (TFT), as an electric signal. In contrast, the indirect-type FPD utilizes a scintillator to convert X-ray energy into a light, which is converted into an electric charge by a photoelectric conversion element, and then the electric charge is read by a readout element, e.g. a thin film transistor (TFT), as an electric signal. In either method, information of the imaged object, which is being collected on the surface of the detector, is read as the information that is spacially sampled according to the pitch of the readout element (known as a "detector pitch" hereinafter).

As shown in FIG. 16, when an imaged object 110 is irradiated by an X ray 111, a portion of the X ray 111 is absorbed by the imaged object 110, but the rest of the X ray 111 is not absorbed and reaches a detector 102 as a transmission X ray 112. In addition to the transmission X ray 112 that passes through the imaged object 110, a noise component, called a scattered ray 113, is also released from the imaged object 110. The scattered ray 113 reduces the SN ratio (Signal to Noise ratio) or the contrast of the imaging information of the imaged object 110, which is transmitted by the transmission X ray 112. In this situation, a grid 101 is usually used to eliminate the scattered ray as much as possible.

A structure of the grid 101 includes X-ray shielding materials 103 and intermediate materials 104, wherein the X-ray shielding materials 103 are stripe-like and respectively separated by an interval to accommodate the intermediate materials 104. Because the scattered ray 113 is absorbed by the X-ray shielding materials 103, the scattered ray 113 does not reach the detector 102. Thus, the SN ratio and the contrast of the image information can be enhanced. However, in a situation in which a secondary scattered ray 116 occurs in the intermediate materials 104, the secondary scattered ray 116 cannot be completely eliminated.

Generally speaking, the grid ratio or grid density is used as a value that represents the scattered-ray-elimination capability of the grid. The grid ratio and grid density are determined by the thickness C and the height A of the X-ray shielding materials and the thickness B of the intermediate materials, as shown in FIG. 17. Grid ratio is defined as r=A/B and grid density is defined as N=1/(B+C) [lp/cm]. The foregoing values are determined based on the types of the detectors and the usages thereof.

Grids are categorized into two types, for example, a movable grid and a fixed grid. In terms of the movable grid, the grid is simultaneously moved with the X-ray radiation in a direction of the grid stripes or in a direction perpendicular to the grid stripes, so as to avoid forming a fixed pattern of the grid in the image. In terms of the fixed grid, the imaging process is carried out with the grid fixed on the detector. When the fixed grid is used in the imaging process, the imaged object information that reaches the detector includes the grid stripes with the fixed pattern.

When using the movable grid, the grid stripes with the fixed pattern are not included. However, the X-ray shielding materials may cause a cutoff during the movement, which results in the deficiency of X ray and impairs the image quality. Also, a means is required to mechanically move the grid, and consequently, the device would be larger in size and the production costs thereof is increased. Furthermore, vibration caused by the movement and electric noise generated by the motor have great negative influence on the image.

On the other hand, when the fixed grid is used, it is necessary to perform a correction on the fixed pattern of the grid stripes. If the relative positions of the grid and the X-ray flat panel detector remain definite, the correction data that has been obtained in advance can be used to perform the subsequent correction.

However, when the grid is installed on or dismantled from the X-ray flat panel detector, misalignment may occur. As a result, the correction data that has been obtained in advance cannot be used for correction.

Accordingly, the following techniques have been disclosed: a marker is disposed on the grid, or an image signal is relied on to determine the position of the shadow of the X-ray shielding materials 103 to thereby infer the relative position relationship between the grid and the X-ray flat panel detector, and the correction is performed on the fixed pattern of the grid stripes based on the relative position relationship (see Patent References 1-3, for instance).

Patent Reference 1: JP 2001-134748
Patent Reference 2: U.S. Pat. No. 5,581,592
Patent Reference 3: U.S. Pat. No. 5,291,539

However, the shape of the shadow of the marker is subject to change with the position, etc. of the X-ray focal point. Due to the influence of noise, etc., the shadow may not have the same shape as the marker. Furthermore, even though an extension of the shadow of the marker can be determined by the processing threshold values of each pixel value, the value that should be set as the threshold value may vary according to imaging conditions and status of the imaged object. Therefore, it is difficult to determine the extension of the shadow, and as a result, the position of the marker may not be determined correctly.

SUMMARY OF THE INVENTION

The invention is to resolve at least one of the foregoing issues and to thereby perform proper correction on fixed patterns of grid stripes.

In order to solve the aforementioned problems, a two-dimensional radiation detector of the invention includes an X-ray irradiating unit having an X-ray focal point; a scattered-ray-elimination grid that includes a plurality of X-ray shielding foils arranged along a horizontal direction or a vertical direction; an X-ray detecting portion for detecting an X ray irradiated from the X-ray irradiating unit through the scattered-ray-elimination grid and outputting a two-dimensional signal; a marker formed by an X-ray shielding material disposed on the scattered-ray-elimination grid; a statistic calculation unit for calculating a statistical value of the two-dimensional signal in a plurality of predetermined observed regions; a correction parameter calculation unit for calculating a correction parameter based on the statistic value; and a moire-elimination unit for removing a shadow of the scattered-ray-elimination grid in an X-ray image by image processing based on the correction parameter. The plurality of observed regions include a group of observed regions having the following relationship. When there is a change in a relative position relationship among the X-ray focal point, the scattered-ray-elimination grid, and the X-ray detecting portion, and the shadow of the marker moves in an arrangement direction of the X-ray shielding foils, the increasing or decreasing trend of the statistical value of one observed region is opposite to the increasing or decreasing trend of the statistical value of another observed region. The correction parameter calculation unit calculates the correction parameter based on a difference between the statistical values acquired from the groups of observed regions.

In addition, when the shadow of the marker overlaps with the image, it is preferable the overlapping is minimized. However, in order to determine the position of the shadow of the marker, the marker having a certain size is required. Accordingly, the invention provides a plurality of markers, and the observed regions are respectively determined based on each of the markers.

Furthermore, it is preferable that the shadow of the marker does not overlap with the image. Accordingly, in the invention, the two-dimensional signal includes an image signal and unused signals around the image signal, and the statistical value is obtained based on the unused signals.

Moreover, the influence of signal strength cannot be eliminated simply by calculating a difference between the statistical values obtained from the group of observed regions. Accordingly, the invention is characterized in that when the statistical values acquired from the group of observed regions are set as Sa and Sb, the correction parameter is set as Rg, and Rg=(Sa−Sb)/(Sa+Sb).

In order to reduce the influence of the noise, the invention carries out a noise-elimination by adding or averaging the statistical values.

According to the features of the invention, the amount of movement of the marker can be accurately calculated. Even if the relative positions of the X-ray tube, the grid, and the X-ray detecting portion change, the shadow of the grid can still be eliminated effectively. Since a plurality of markers are disposed, the size of each of the markers can be reduced. Furthermore, because the markers are configured to project a shadow on the regions of unused signals, the effects of the invention are achieved without affecting the obtained image. Additionally, the influence of signal strength can be eliminated and the statistical value that corresponds to the misalignment can be calculated in any imaging condition. Therefore, the shadow of the grid can be effectively removed in spite of the imaging conditions, and the influence of noise can be eliminated by performing an adding or averaging calculation.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Embodiments of the invention are described below with reference to the accompanying drawings.

First Embodiment

Figure 1:
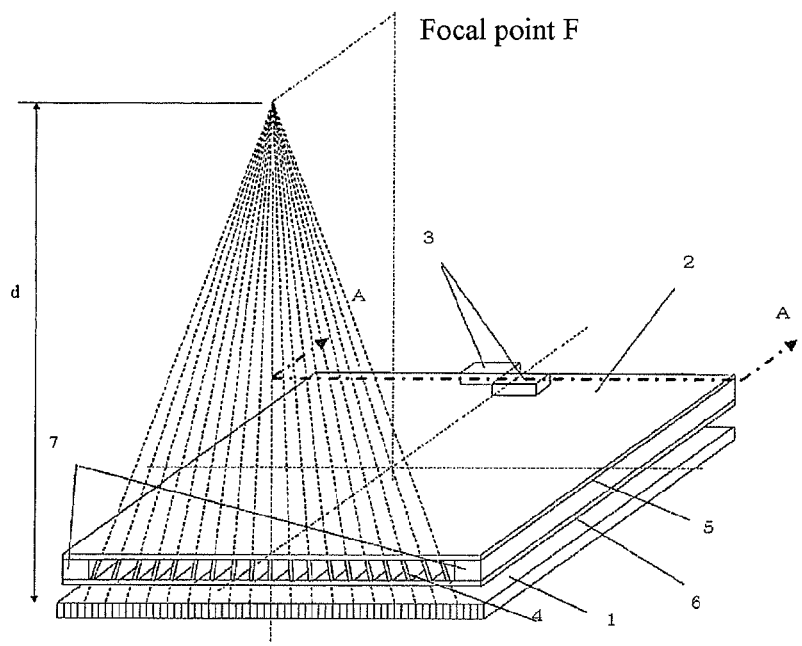
FIG. 1 is a schematic perspective view of a radiation imaging device according to the First Embodiment.
Figure 2:
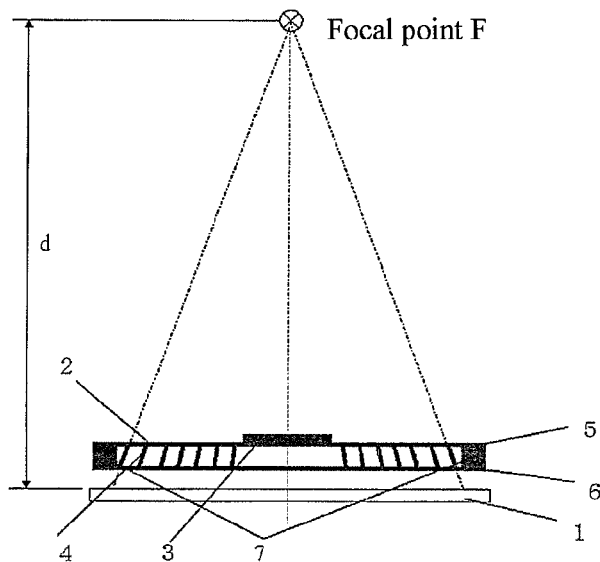
FIG. 2 is a schematic cross-sectional view along Line A-A in FIG. 1.
Figure 3:
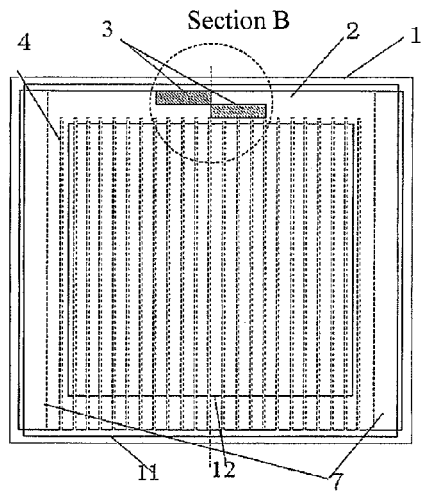
FIG. 3 is a schematic top view of FIG. 1.

FIG. 1 is a schematic perspective view, illustrating a marker 3 disposed integrally with a scattered-X-ray-elimination grid 2, in contrast to a structure formed by an X-ray flat panel detector 1 and the grid 2 in the First Embodiment of the invention. FIG. 2 is a schematic cross-sectional view along Line A-A in FIG. 1, and FIG. 3 is a schematic top view of FIG. 1.

According to the present embodiment, the X-ray shielding foils 4 that constitute the grid 2 are pointed towards an X-ray focal point F in an X-ray tube (not shown in the drawings). Further in a distance d between the X-ray focal point F and the X-ray flat panel detector 1, the X-ray shielding foils 4 are respectively spaced by a pitch that is an integer multiple of each pixel arranged on the surface of X-ray flat panel detector 1. In the embodiment shown in FIG. 1, the pitch between two neighboring X-ray shielding foils 4 is three times of each pixel on the surface of the X-ray flat panel detector 1. In fact, the separation lines, as shown in the cross-sectional view of FIG. 1, do not exist in the X-ray flat panel detector 1, and a pixel pitch is determined by a pitch of TFT (Thin Film Transistor) element. The separation lines are depicted to better illustrate the embodiment. A top end face and a bottom end face of each of the X-ray shielding foils 4 are supported by a top covering material 5 and a bottom covering material 6. Specifically, the top covering material 5 and the bottom covering material 6 use a thin carbon fiber sheet or a thin aluminum plate that provides X-ray transmissibility. On two ends of the X-ray shielding foils 4, spacers 7 are inserted and adhered to the top covering material 5 and the bottom covering material 6.

In this embodiment, the marker 3 is integrally disposed with the grid 2 on the top covering material 5. The marker 3 shields a portion of two observed signal regions of the X-ray flat panel detector 1 from an X ray and masks a portion of the two observed regions.

Herein, the X-ray tube is equivalent to an X-ray irradiating unit of the invention; the grid 2 is equivalent to a scattered-ray-elimination grid of the invention; and the X-ray flat panel detector 1 is equivalent to an X-ray detecting portion of the invention.

With reference to FIG. 3, a signal-acquisition region includes an X-ray conversion film, wherein the signal is capable for substantially operating an x-ray conversion film and a TFT, and an imaging region 12 positioned in an inner portion of the signal-acquisition region 11 for conducting imaging and diagnosis. The X-ray shielding foils 4 of the grid 2 are configured to completely mask the imaging region 12, but it should be noted that the invention is not limited thereto. With respect to the relative position relationship among the X-ray flat panel detector 1, the X-ray focal point F, and the grid 2, the marker 3 is disposed in a way that the shadow of the marker 3 reaches the outside of the imaging region 12 and the inside of the signal-acquisition region 11. Relative to the grid 2, the marker 3 is configured in a way that the shadow thereof is prevented from reaching the above position of the X-ray shielding foils 4 but reaches an upper central portion of the top covering material 5.

Figure 4:
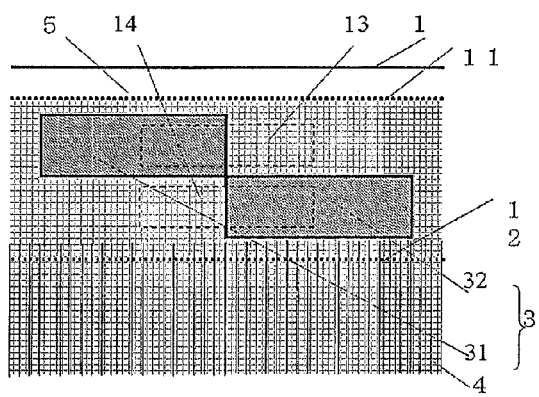
FIG. 4 is a schematic detailed view of Section B in FIG. 3.

FIG. 4 is a schematic perspective view that provides further details about the position relationship in Section B of FIG. 3. The marker 3 is formed with a shielding material mask 31 and a shielding material mask 32. As shown in FIG. 4, the shielding material masks 31 and 32 are disposed and attached with the upper central portion of the top covering material 5. Specifically, the material of the shielding material masks 31 and 32 includes molybdenum (Mo), tungsten (W), lead (Pb), tantalum (Ta), or an alloy having any of the foregoing elements, that have a larger atomic number and a great X-ray absorption, as a main component. Thus, when being irradiated by an X ray, no signal is generated in an area masked by the shielding material masks 31 and 32 in the X-ray flat panel detector 1.

Meanwhile, an observed signal region 13 and an observed signal region 14 are set in the signal-acquisition region 11 of the X-ray flat panel detector 1. According to the condition as depicted in FIG. 4, because a portion of the observed signal regions 13 and 14 is shielded by the shielding material masks 31 and 32 of the marker 3, signals can only be obtained from the unshielded area when being irradiated by an X ray.

The observed signal regions 13 and 14 are equivalent to the observed regions of the invention. Moreover, the signal acquired by the imaging region 12 is equivalent to an image signal of the invention, and the signal acquired by the signal-acquisition region 11 outside the imaging region 12 is equivalent to an unused signal of the invention.

Meanwhile, a signal value obtained from the observed signal region 13 is defined as Sai (i: pixel number of the X-ray flat panel detector 1 existing in the observed signal region 13), and a summation value of Sai is defined as Sa=ΣSai. Furthermore, a signal value from the observed signal region 14 is defined as Sbi (i: pixel number of the X-ray flat panel detector 1 that exists in the observed signal region 14), and an summation value of Sbi is defined as Sb=ΣSbi. Accordingly, if Rg=(Sa−Sb)/(Sa+Sb) is defined, the Rg value is uniquely corresponding to the relative position relationship between the X-ray flat panel detector 1 and the marker 3, formed by the shielding material masks 31 and 32, in a direction perpendicular to the arrangement of the X-ray shielding foils 4. Moreover, because the marker 3 is integrally disposed with the grid 2, the Rg value uniquely corresponds to the relative position relationship between the grid 2 and the X-ray flat panel detector 1 in the direction perpendicular to the arrangement of the X-ray shielding foils 4.

The aforementioned summation value is equivalent to a statistical value of the invention.

Because the grid 2 is used as a fixed grid in the invention, when an X-ray imaging is carried out, information of the imaged object passes through the grid 2 and reaches the X-ray flat panel detector 1, and the information of the imaged object includes a fixed pattern of grid stripes, which is the shadow of the X-ray shielding foils 4. To eliminate the shadow, correction is usually required. Thus, in the situation that a set distance between the X-ray focal point F and the X-ray flat panel detector 1 is d, and with respect to anyone of the relative position relationships of the grid 2 and the X-ray flat panel detector 1, correction data is obtained in advance and used to perform correction on the data acquired during the actual imaging.

However, in the application thereof as a general device, the grid 2 may be dismantled from or installed onto the X-ray flat panel detector 1 according to the imaged object during an X-ray imaging. When the grid 2 is dismantled, the relative position of the grid 2 and the X-ray flat panel detector 1 may become misaligned, from which the correction data has been obtained. Misalignment that occurs in the direction perpendicular to the arrangement of the X-ray shielding foils 4 is especially obvious.

Figure 5:
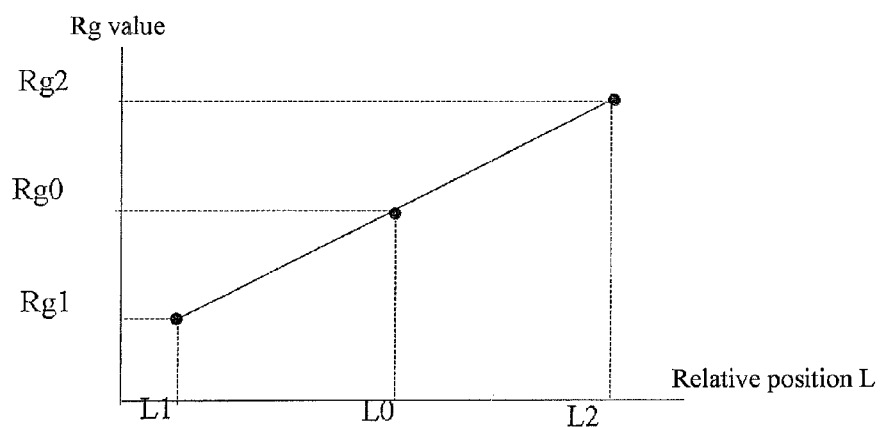
FIG. 5 is a table, illustrating the relationship between a Rg value and a relative position L of a grid 2 with respect to an X-ray flat panel detector 1.

Therefore, when the grid 2 is dismantled, the misalignment in the direction perpendicular to the arrangement of the X-ray shielding foils 4 is anticipated, and the correction data that corresponds to the Rg value of the misalignment status is acquired in advance to provide a data table accordingly. As in the example shown in FIG. 5, wherein FIG. 5 illustrates a relationship between a relative position L of the grid 2 with respect to the X-ray flat panel detector 1 and the Rg value. Each of the Rg values has correction data corresponding thereto.

Accordingly, by installing a means to monitor the relative position relationship between the grid 2 and the X-ray flat panel detector 1, the relative position relationship can be inferred based on the calculated value Rg, and a correction parameter thereof can be used to easily correct the inaccuracy that may occur due to the misalignment.

Figure 6:
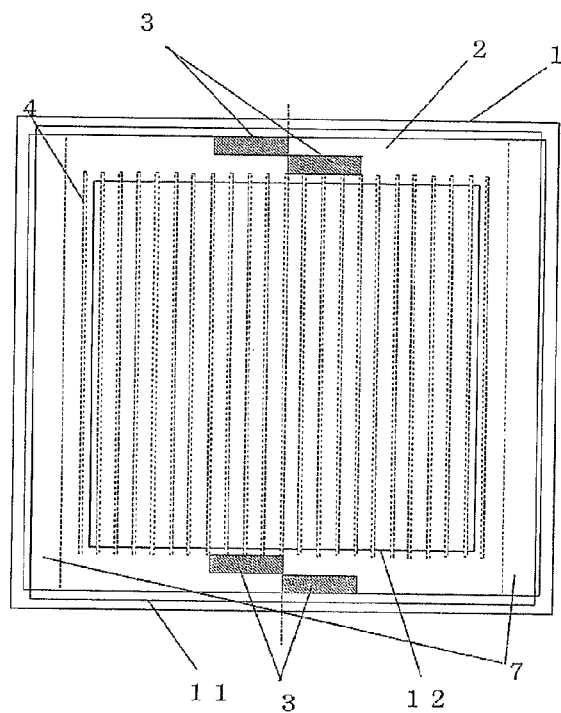
FIG. 6 is a schematic top view of another example of the First Embodiment.

In addition, FIG. 6 depicts another modified embodiment. As shown in FIG. 6, markers 3 are respectively disposed on an upper central portion and a lower central portion of the top covering material 5 to serve as the means for monitoring the relative position relationship between the grid 2 and the X-ray flat panel detector 1. In this situation, Rgu and Rgl values are respectively obtained from the markers 3, and addition average value (Rg ave.) of Rgu and Rgl is set to Rg ave.=(Rgu+Rgl)/2. The Rg ave. value can be utilized to uniquely correspond to the relative position relationship between the grid 2 and the X-ray flat panel detector 1 in the direction perpendicular to the arrangement of the X-ray shielding foils 4.

Moreover, three or more of the markers 3 can be disposed as the means to monitor the relative position relationship between the grid 2 and the X-ray flat panel detector 1.

In the above examples, all of the markers 3 are disposed to prevent from reaching the above position of the X-ray shielding foils 4. However, when the Rg value uniquely corresponds to the relative position relationship between the grid 2 and the X-ray flat panel detector 1 in the direction perpendicular to the arrangement of the X-ray shielding foils 4, the markers 3 can also be positioned above the X-ray shielding foils 4.

Further to the above, if the grid 2 is a scattered-X-ray-elimination grid, a two-dimensional radiation detector with very high sensitivity can be achieved. The scattered-X-ray-elimination grid is formed by the following approach: guide-slit plates having a plurality of guide slits formed thereon are oppositely and fixedly disposed; a plurality of metal foils, which serves as X-ray absorption materials, are disposed between the guide slits and inserted into the guide slits in parallel to a primary X ray, and the metal foils are separated by a predetermined distance and parallel to each other; in a status that two ends of each of the metal foils are inserted into the opposite guide slits on the guide-slit plates, a tension-applying device applies a tension from the outer side of the guide slits to maintain one or two ends of each of the metal foils; thin plates containing a light element are used as grid covers to respectively cover an X-ray incident side and an X-ray emergent side of each of the metal foils and is bonded thereon; then, the tension-applying device and a fixture device of the metal foils are removed; two ends of the metal foils are cut off from the inner side of the guide-slit plates; and the metal foils are removed from the guide-slit plates and form the scattered-ray-elimination grid.

However, due to the difficulty of the fabrication process, the high-density grid cannot be formed. Thus, when carrying out an X-ray imaging, the information of the imaged object that passes through the grid 2 and reaches the X-ray flat panel detector 1 includes more fixed patterns of grid stripes that are caused by the shadow of the X-ray shielding foils 4. In the above situation, the invention can easily carry out the correction.

Second Embodiment

Figure 7:
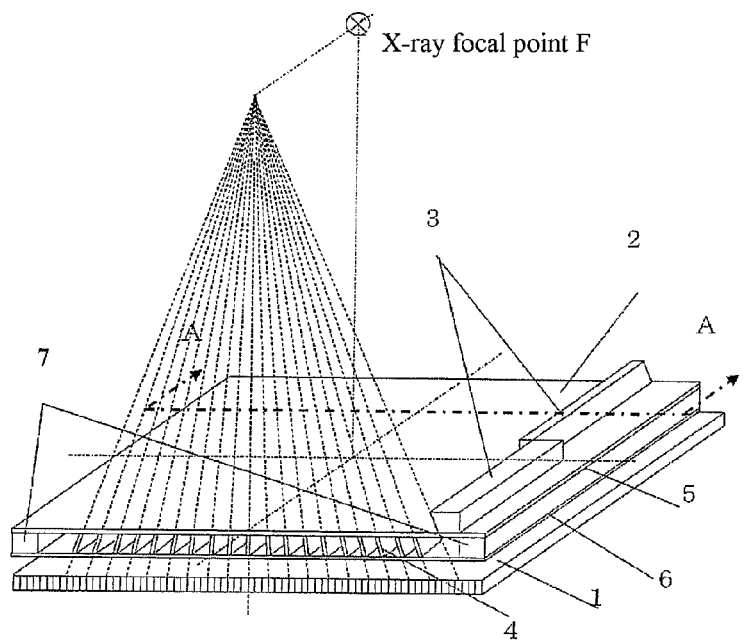
FIG. 7 is a schematic perspective view of a radiation imaging device according to the Second Embodiment.
Figure 8:
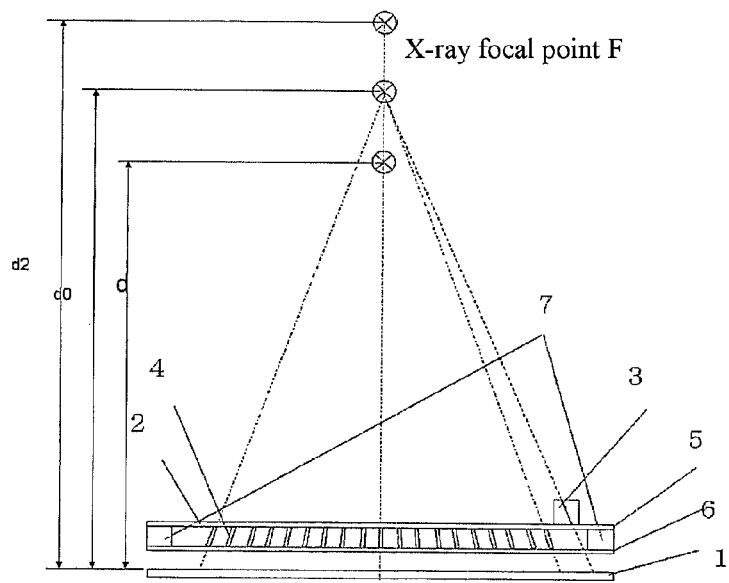
FIG. 8 is a schematic cross-sectional view along Line A-A in FIG. 7.
Figure 9:
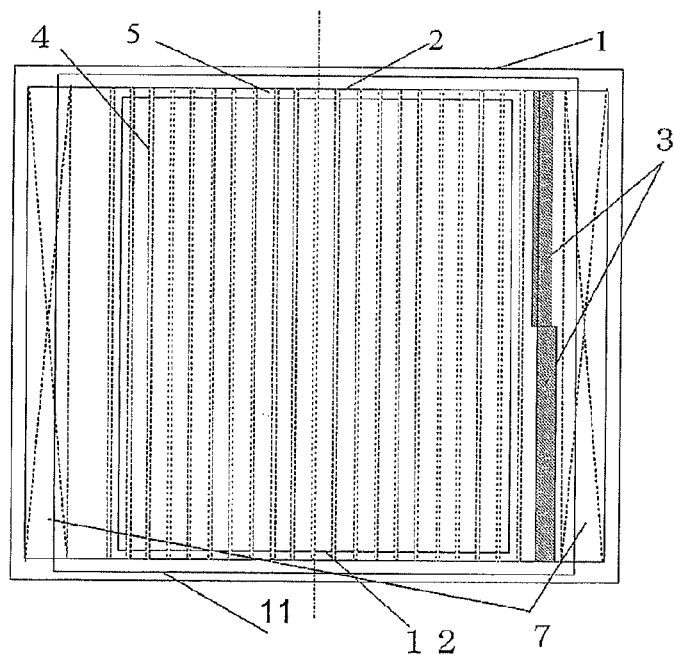
FIG. 9 is a schematic top view of FIG. 7.

FIG. 7 is a schematic perspective view, illustrating a configuration of a marker 3 being disposed integrally with a scattered-X-ray-elimination grid 2, in contrast to a structure formed by the X-ray flat panel detector 1 and the grid 2 in the Second Embodiment of the invention. FIG. 8 is a schematic cross-sectional view along Line A-A in FIG. 7, and FIG. 9 is a schematic top view of FIG. 7.

In this embodiment, the X-ray shielding foils 4 that form the grid 2 are pointed towards the X-ray focal point F, and when a relative distance d between the X-ray focal point F and the X-ray flat panel detector 1 is d0 (determined position), the X-ray shielding foils 4 are spaced by a pitch that is an integer multiple of the pitch between the pixels arranged on the surface of the X-ray flat panel detector 1. According to the embodiment in FIG. 7, the pitch between two neighboring X-ray shielding foils is three times of the pitch between pixels on the surface of the X-ray flat panel detector 1. In fact, the separation lines, as shown in the cross-sectional view of FIG. 7, do not exist in the X-ray flat panel detector 1, and a pixel pitch is determined by the pitch of the TFT elements. The separation lines are depicted to better illustrate the embodiment. A top end face and a bottom end face of each of the X-ray shielding foils 4 are supported by a top covering material 5 and a bottom covering material 6. Specifically, the top covering material 5 and the bottom covering material 6 includes a thin carbon fiber sheet or a thin aluminum plate that provides X-ray transmissibility. On two ends of the X-ray shielding foils 4, spacers 7 are inserted and attached to the top covering material 5 and the bottom covering material 6.

According to this embodiment, the marker 3 is positioned side by side on the right end of the X-ray shielding foils 4 and integrally disposed with the grid 2 on the top covering material 5. In addition, the marker 3 includes an X-ray shielding plate 31 and an X-ray shielding plate 32. A cross-sectional view of the X-ray shielding plate 31 and the X-ray shielding plate 32 includes a shape, which has a border that is in accordance with a line connecting the X-ray focal point F to end pixels of the X-ray flat panel detector 1.

Furthermore, the marker 3 shields a portion of two observed signal regions on the right end of the X-ray flat panel detector 1 from an X ray and masks a portion of the two observed regions.

Referring to FIG. 9, the X-ray flat panel detector 1 substantially includes a X-ray conversion film and a signal-acquisition region 11 which acquires a signal of an operating and TFT, and an imaging region 12 positioned in an inner portion of the signal-acquisition region 11 for carrying out imaging and diagnosis. Of course, the X-ray shielding foils 4 of the grid 2 are configured to completely mask the imaging region 12. In addition, according to this embodiment, the marker 3 is located outside the imaging region 12 but inside a right end of the signal-acquisition region 11, with respect to the X-ray flat panel detector 1. With respect to the grid 2, the marker 3 is configured and connected to prevent from reaching the above position of the X-ray shielding foils 4 but reaches the right end of the top covering material 5.

Figure 10:
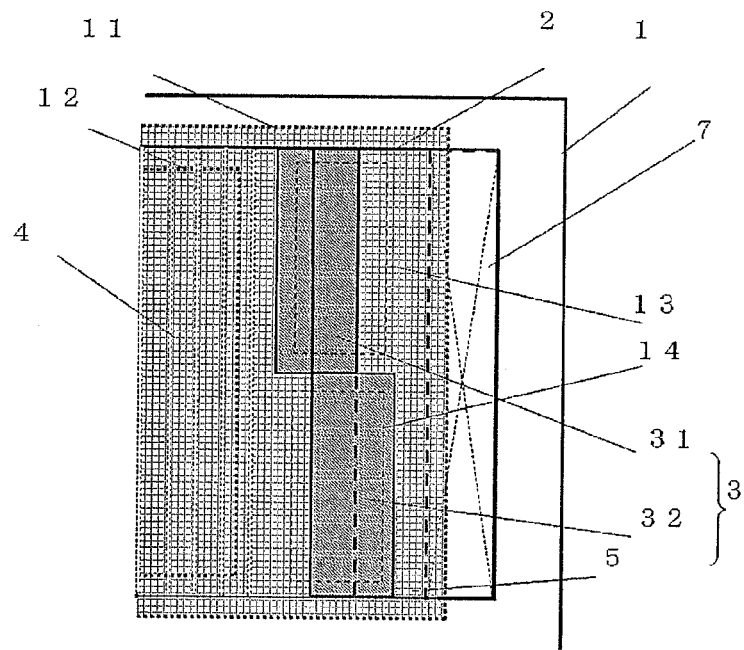
FIG. 10 is a schematic detailed view around a marker 3 in FIG. 9.

FIG. 10 is a schematic perspective view proximal to the marker 3 to provide more details about the position relationship of FIG. 9. The marker 3 is constituted by a X-ray shielding plate 31 and a X-ray shielding plate 32. More specifically, a material of the X-ray shielding plates 31 and 32 includes molybdenum, tungsten, lead, tantalum, or an alloy having any of the foregoing elements as a main component, which has a larger atomic number and greater X-ray absorption. Therefore, when being irradiated by an X ray, an area shielded by the X-ray shielding plates 31 and 32 in the X-ray flat panel detector 1 does not generate any signal.

Meanwhile, an observed signal region 13 and an observed signal region 14 are set in the signal-acquisition region 11 of the X-ray flat panel detector 1. In the status shown in FIG. 10, when being irradiated by an X-ray, because a portion of the observed signal regions 13 and 14 is shielded by the X-ray shielding plates 31 and 32 of the marker 3, signals can only be obtained from the unshielded area.

Figure 11:
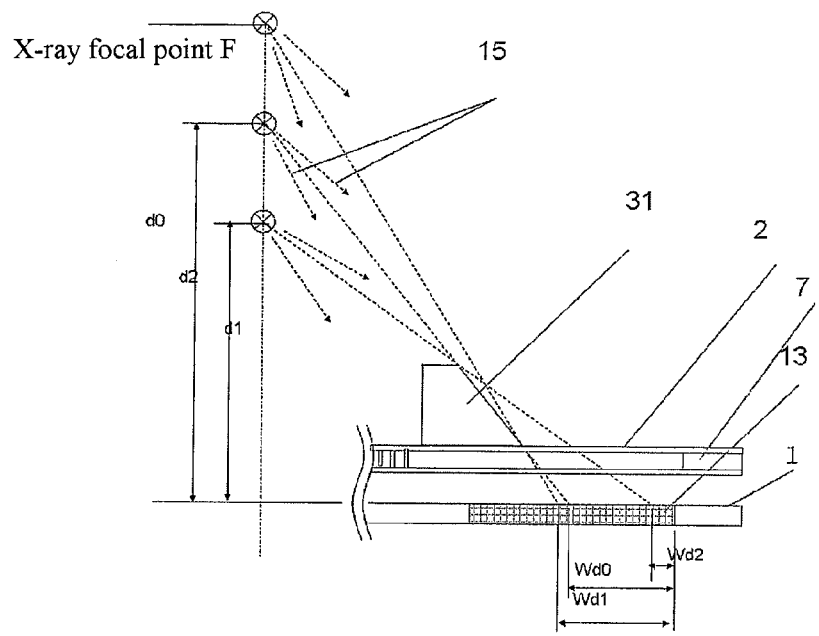
FIG. 11 illustrates incident X rays towards an observed signal region 13 in the Second Embodiment.

For the application of the actual device, as shown in FIG. 11, the predetermined relative distance d0 between the X-ray focal point F and the X-ray flat panel detector 1 may change sometimes. With respect to the X-ray shielding plate 31, FIG. 11 illustrates an X-ray incident towards the observed signal regions 13 and 14 when the relative distance is changed to d1 and d2. With respect to the X-ray shielding plate 32, FIG. 12 illustrates an X-ray incident towards the observed signal regions 13 and 14 when the relative distance is changed to d1 and d2.

In FIG. 11, an X-ray 15 is emitted from the X-ray focal point F and passes around the marker 3 to irradiate the pixels on the X-ray flat panel detector 1. At the same time, a signal is generated in an area, which is not masked by the X-ray shielding plate 31 and is inside the observed signal region 13. As depicted in FIG. 11, when the relative distance is d0, an area Wd0 generates a signal; when the relative distance is d1, an area Wd1 generates a signal; and when the relative distance is d2, an area Wd2 generates a signal. A signal value from the observed signal region 13 at this moment is defined as Sxi (i: pixel number of the X-ray flat panel detector 1 that exists in the observed signal region 13), and an addition value of Sxi is defined as Sx=ΣSxi. If the relative distance d becomes shorter, the summation value Sx is decreased; if the relative distance d becomes longer, the summation value Sx is increased.

Figure 12:
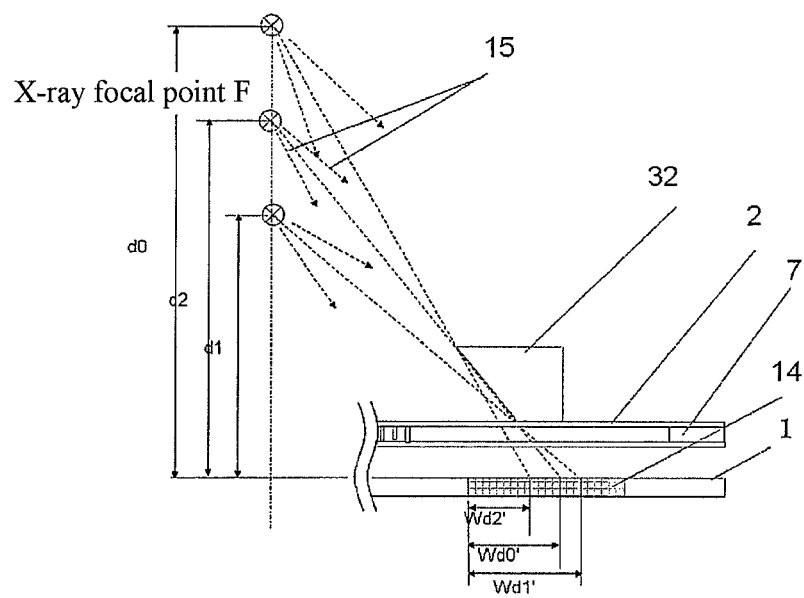
FIG. 12 illustrates incident X rays towards an observed signal region 14 in the Second Embodiment.

Additionally, referring to FIG. 12, an X-ray 15 is emitted from the X-ray focal point F and passes around the marker 3 to irradiate the pixels on the X-ray flat panel detector 1. At the same time, a signal is generated in an area, which is inside the observed signal region 14 and is not masked by the X-ray shielding plate 32. As shown in FIG. 12, when the relative distance is d0, a signal is generated in an area Wd0'; when the relative distance is d1, a signal is generated in an area Wd1'; and when the relative distance is d2, a signal is generated in an area Wd2'. A signal value from the observed signal region 14 at this moment is defined as Syi (i: pixel number of the X-ray flat panel detector 1 that exists in the observed signal region 14), and a summation value of Syi is defined as $Sy=\Sigma Syi$. If the relative distance d becomes shorter, the summation value Sy increases; if the relative distance d becomes longer, the summation value Sy decreases.

Accordingly, if $Rf=(Sx-Sy)/(Sx+Sy)$ is defined, the Rf value uniquely corresponds to the relative distance d, that is the relative position relationship between the X-ray focal point F and the X-ray flat panel detector 1.

Figure 13:
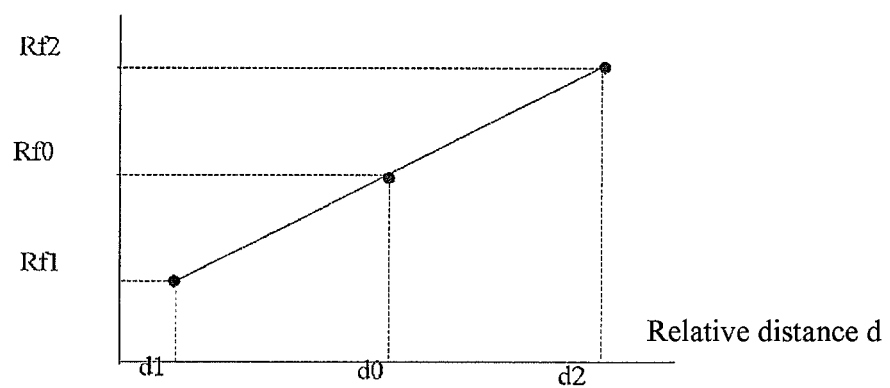
FIG. 13 is a table, showing the relationship between a Rf value and a relative distance d between an X-ray focal point F and an X-ray flat panel detector 1.

Alternatively speaking, variation of the relative distance d between the X-ray focal point F and the X-ray flat panel detector 1 is predicted beforehand, and correction data that corresponds to the Rf value at the variation is obtained to provide a data table. Referring to the embodiment in FIG. 13, in which a relationship between the Rf value and the relative distance d of the X-ray focal point F and the X-ray flat panel detector 1 is presented. The correction data is obtained in correspondence to each Rf value.

Therefore, by installing a means to monitor the relative position relationship between the X-ray focal point F and the X-ray flat panel detector 1, even if the relative distance d between the X-ray focal point F and the X-ray flat panel detector 1 changes, the relative position relationship thereof can still be determined based on the Rf value, and the correction parameter thereof can be used to easily correct the inaccuracy caused by the misalignment of the X-ray focal point F and the X-ray flat panel detector 1.

Figure 14:
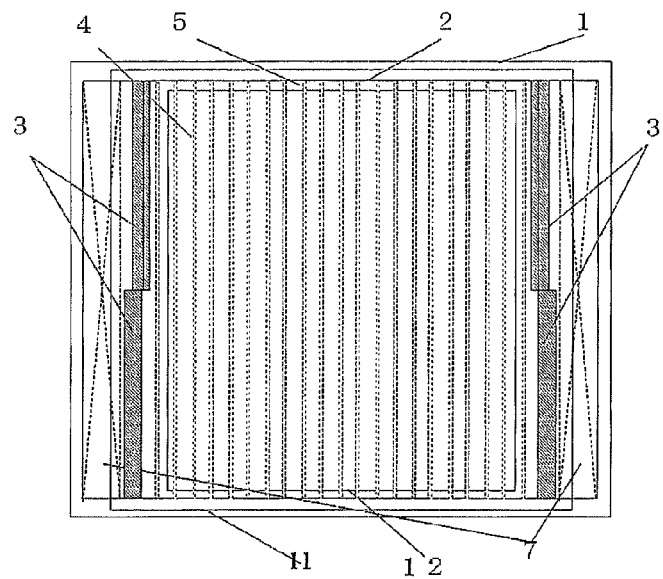
FIG. 14 is a schematic top view of another example of the Second Embodiment.

FIG. 14 further illustrates another modified embodiment. In FIG. 14, markers 3 are positioned side by side on the left and right ends of the X-ray shielding foils to serve as a means for monitoring the relative position relationship between the X-ray focal point F and the X-ray flat panel detector 1, and the markers 3 are integrally disposed with the grid 2 on the top covering material 5. In this situation, Rfr and Rfl values are respectively obtained from the markers 3, and the average value (Rg ave.) of Rfr and Rfl is defined as Rg ave.=(Rfr+Rfl)/2. Rg ave. is used to uniquely correspond to the relative position relationship between the X-ray focal point F and the X-ray flat panel detector 1.

Moreover, three or more of the markers 3 can be disposed as the means to monitor the relative position relationship between the X-ray focal point F and the X-ray flat panel detector 1.

In the above embodiments, all the markers 3 are integrally disposed with the grid 2 on the top covering material 5. However, in the case that the calculated value Rf uniquely corresponds to the relative position relationship between the X-ray focal point F and the X-ray flat panel detector 1, the aforesaid markers 3 can be located at any position other than the top covering material 5.

In any of the above embodiments, more than one marker 3 is disposed. However, as shown in FIG. 15, the invention can include only one marker 3.

Figure 15:
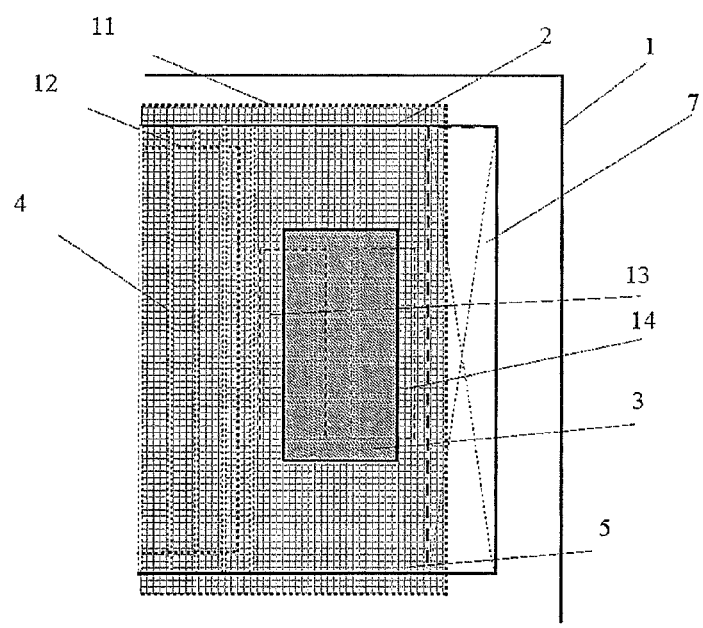
FIG. 15 illustrates an example that includes only one marker 3.
Figure 16:
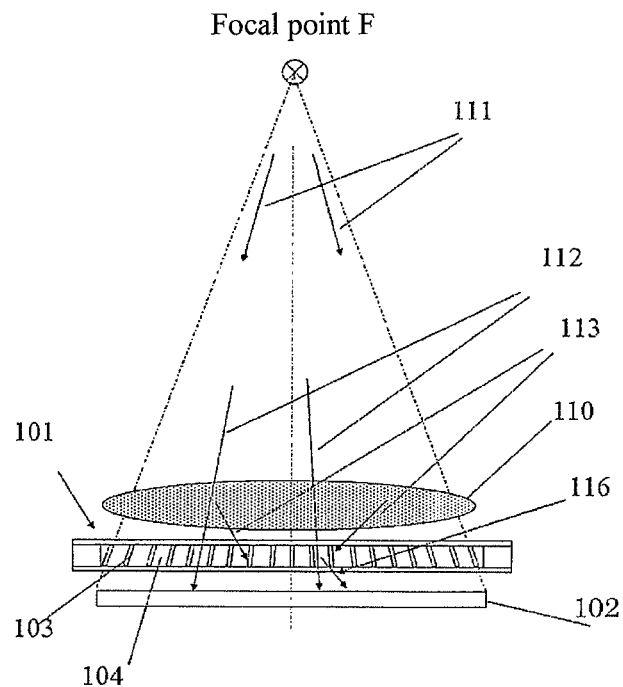
FIG. 16 is a schematic view of a conventional two-dimensional radiation detector.
Figure 17:
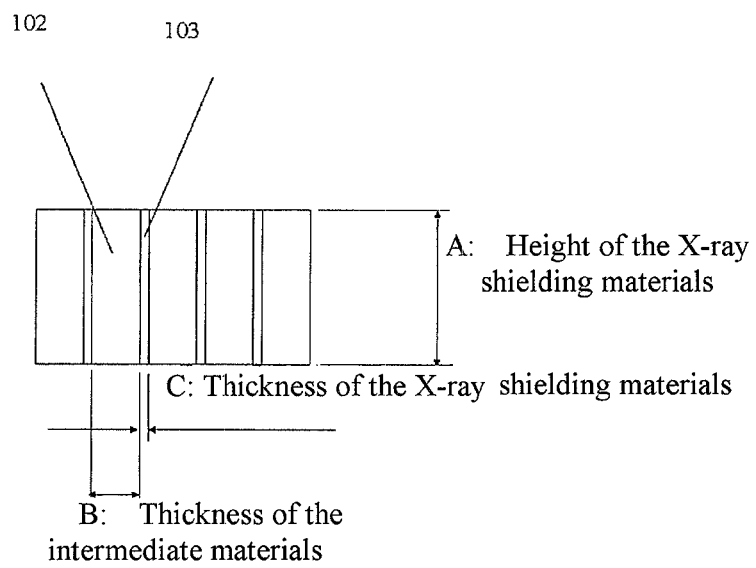
FIG. 17 depicts the structure of a grid.

FIG. 15 corresponds to FIG. 4 of the First Embodiment and FIG. 10 of the Second Embodiment. For instance, when the grid 2 is misaligned in a direction towards the right, the marker 3 is also misaligned in a direction towards the right. Accordingly, the shadow of the marker 3 also moves in a direction to the right on the X-ray flat panel detector 1. Consequently, as the amount of the X-ray detected in the observed signal region 13 increases, the amount of the X-ray detected in the observed signal region 14 decreases.

Thus, the observed signal regions 13 and 14 are set according to the direction of the misalignment that is to be detected, and the same effects as in the First and Second Embodiments can be achieved.

As described above, one single marker 3 can be installed to achieve the effects of the invention. However, when a plurality of the markers 3 is disposed, the markers 3 can be positioned separately. Thus, the markers 31 and 32 can be disposed in positions of maximum distance, such as the left and the right ends of the grid 2. Because the amount of movement of the shadow with respect to the misalignment is large, multiple signals of opposite increasing/decreasing directions can be detected. By calculating the difference between the multiple signals, larger variation of the signals with respect to the misalignment can be obtained. That is, S/N can be increased.

Although the invention has been described with reference to the above embodiments, it is apparent to one of ordinary skill in the art that modifications to the described embodiments may be made without departing from the spirit of the invention. Accordingly, the scope of the invention is defined by the attached claims not by the above detailed descriptions.

What is claimed is:

1. A two-dimensional radiation detector, comprising:
an X-ray irradiating unit, having an X-ray focal point;
a scattered-ray-elimination grid, comprising a plurality of X-ray shielding foils arranged along a horizontal direction or a vertical direction;
an X-ray detecting portion, detecting an X ray irradiated from the X-ray irradiating unit through the scattered-ray-elimination grid and outputting a two-dimensional signal;
a marker, formed by an X-ray shielding material disposed on the scattered-ray-elimination grid;
a statistical calculation unit, calculating a statistical value of the two-dimensional signal in a plurality of predetermined observed regions;
a correction parameter calculation unit, calculating a correction parameter based on the statistical value; and
a moire-elimination unit, removing a shadow of the scattered-ray-elimination grid in an X-ray image by an image processing based on the correction parameter,
wherein the plurality of predetermined observed regions comprises a group of observed regions having a following relationship:
when a relative position relationship among the X-ray focal point, the scattered-ray-elimination grid, and the X-ray detecting portion changes, and a shadow of the marker moves in an arrangement direction of the X-ray shielding foils, the increasing or decreasing trend of the statistical value of one observed region of the group of observed regions is opposite to the increasing or decreasing trend of the statistic value of another observed region of the group of observed regions.

2. The two-dimensional radiation detector as claimed in claim 1, wherein the number of the marker is plural, and the observed regions are determined respectively according to each of the markers.

3. The two-dimensional radiation detector as claimed in claim 1, wherein the two-dimensional signal comprises an image signal and unused signals around the image signal, and the statistical value is obtained based on the unused signals.

4. The two-dimensional radiation detector as claimed in claim 1, wherein $Rg=(Sa-Sb)/(Sa+Sb)$ when the statistical values obtained based on the group of observed regions are set as Sa and Sb respectively, and the correction parameter is set as Rg.

5. The two-dimensional radiation detector as claimed in claim 1, wherein the statistical values are obtained by performing a summation or an averaging calculation.

* * * * *